(12) United States Patent
Stone

(10) Patent No.: US 6,503,207 B2
(45) Date of Patent: Jan. 7, 2003

(54) MULTI-MODE AUDIOMETRIC DEVICE AND ASSOCIATED SCREENING METHOD

(75) Inventor: Robert T. Stone, Sunnyvale, CA (US)

(73) Assignee: Natus Medical, Inc., San Carlos, CA (US)

( * ) Notice: Subject to any disclaimer, the term of this patent is extended or adjusted under 35 U.S.C. 154(b) by 153 days.

(21) Appl. No.: 09/782,771

(22) Filed: Feb. 13, 2001

(65) Prior Publication Data
US 2001/0034493 A1 Oct. 25, 2001

Related U.S. Application Data
(60) Provisional application No. 60/182,277, filed on Feb. 14, 2000.

(51) Int. Cl.[7] .................................................. A61B 5/00
(52) U.S. Cl. .......................................... 600/559; 73/585
(58) Field of Search ................................ 600/544, 545, 600/559, 379, 382, 383; 73/585, 587

(56) References Cited

U.S. PATENT DOCUMENTS

| 4,374,526 | A |   | 2/1983  | Kemp |
|-----------|---|---|---------|------|
| 4,884,447 | A |   | 12/1989 | Kemp et al. |
| 5,546,956 | A | * | 8/1996  | Thornton ..................... 600/559 |
| 5,601,091 | A | * | 2/1997  | Dolphin ...................... 600/544 |
| 5,734,827 | A |   | 3/1998  | Thornton et al. |
| 5,954,667 | A | * | 9/1999  | Finkenzeller et al. ........ 600/544 |
| 6,071,246 | A | * | 6/2000  | Sturzebecher et al. ....... 600/559 |
| 6,231,521 | B1| * | 5/2001  | Zoth et al. ................... 128/898 |

FOREIGN PATENT DOCUMENTS

WO    WO 200065983 A1 * 11/2000 ............. A61B/5/00

* cited by examiner

Primary Examiner—Eric F. Winakur
Assistant Examiner—Charles Marmor, II
(74) Attorney, Agent, or Firm—Francis Law Group

(57) ABSTRACT

The disclosure describes a multi-mode audiometric device comprising a stimulus generator adapted to transmit at least one true random stimulus sequence to a subject's inner ear, a first detector for detecting at least one AEP signal having at least a first waveform, a second detector for detecting at least one OAE signal having at least a second waveform; a signal analyzer for analyzing the AEP and OAE signals, the signal analyzer including a first averager for reconstructing the first waveform and a second averager for reconstructing the second waveform; and a synchronizer for synchronizing the stimulus generator and signal analyzer.

7 Claims, 2 Drawing Sheets

MULTI-MODE AUDIOMETRIC DEVICE AND ASSOCIATED SCREENING METHOD

CROSS REFERENCE TO RELATED APPLICATIONS

This application claims benefit under 35 U.S.C. 119 (e) of U.S. Provisional Application No. 60/182,277, filed Feb. 14, 2000.

FIELD OF THE INVENTION

The present invention relates generally to the field of audiometric devices. More particularly, the invention relates to a multi-mode audiometric device and auditory screening method.

BACKGROUND OF THE INVENTION

Language acquisition in infants requires a critical period of hearing capacity, which spans the frequency range of human speech. The critical period extends from birth to about two to three years of age, when infants typically begin to talk with some level of proficiency.

It has however been reported that approximately three to five percent of newborn infants suffer from some degree of hearing impairment. These impairments can be devastating to the social, emotional and intellectual development of the affected infants. Early identification of hearing impairments in infants allows for early intervention to minimize significant speech and language deficiencies.

Infants are, however, usually unable or unwilling to participate in known behavioral auditory examinations. Moreover, delaying auditory screening until infants can verbally respond is often too late for hearing impaired infants and in many instances, results in long term problems.

Federal, state and private agencies have attempted to implement universal auditory screening of infants for over twenty years. A major impediment to the implementation of universal auditory screening of infants has been the cost and complexity associated with the tests. Current infant screening tests are time consuming and require expensive devices and trained specialists to conduct the tests and interpret results. As such, universal auditory screening of infants is presently economically infeasible.

Various entities have developed audiometric devices, which may be usable for screening an infant's hearing. These existing devices generally fall into one of two categories. Devices in the first category are configured to elicit auditory evoked potentials (AEPs), which are electrical responses of cells within the auditory pathway of the brain to an acoustic stimulus. Such devices typically utilize the non-invasive auditory brainstem response (ABR) test for auditory screening of infants. An earphone provides an acoustic stimulus, specifically a brief click or toneburst, to the subject's ear. Electrodes attached to the subject's scalp receive auditory evoked potentials (i.e., response signal(s)) from the scalp, which are recorded as an electroencephalogram waveform. Analysis of these brainwave patterns are used to determine if the auditory system is functioning normally.

Devices in the second category utilize the evoked otoacoustic emission (OAE) test for auditory screening. An earphone provides a brief acoustic stimulus to the subject's ear. A microphone disposed in the subject's ear adjacent the earphone receives an OAE signal from the ear, which is recorded as an acoustic signal. Analysis of the OAE waveform provides an indication of the functional integrity of the middle and inner ear, which together comprise the auditory periphery.

A number of limitations exist with respect to existing audiometric screening devices. One limitation is that virtually all of the existing devices are complicated and require extensive training to operate. Another limitation is that separate devices are required to perform ABR and OAE tests. Yet another limitation is that response signals are susceptible to undesirable artifact components and/or noise, which can emanate from the device itself or the subject (e.g., swallowing, grinding of teeth).

It is therefore an object of the present invention to provide a multi-mode audiometric device and auditory screening method that provides simultaneous, comprehensive ABR and OAE testing through a single, portable device.

It is another object of the present invention to provide a multi-mode audiometric device and auditory screening method that significantly reduces response time (i.e., time to receive a response signal) and, hence, test time.

It is yet another object of the present invention to provide a multi-mode audiometric device and auditory screening method that substantially reduces or eliminates synchronous and sampling artifacts.

SUMMARY OF THE INVENTION

In accordance with the above objects and those that will be mentioned and will become apparent below, the multi-mode audiometric device in accordance with this invention comprises stimulus generating means for transmitting at least one true random stimulus sequence to a subject's inner ear; first detection means for detecting at least one AEP signal, the AEP signal having at least a first waveform; second detection means for detecting at least one OAE signal, the OAE signal having at least a second waveform; signal analyzer means for analyzing the AEP and OAE signals, the signal analyzer means including first averager means for reconstructing the first waveform and second averager means for reconstructing the second waveform; and synchronization means for synchronizing the stimulus generating means and the signal analyzer means.

The method of testing the hearing of a subject in accordance with the invention comprises (i) presenting at least one true random stimulus sequence to said subject's inner ear, (ii) detecting at least one AEP signal, the AEP signal having at least a first waveform, the first waveform including a first set of AEP signal data, (iii) detecting at least one OAE signal, the OAE signal having at least a second waveform, the second waveform including a first set of OAE signal data, (iv) recording the AEP and OAE signals, (v) sampling the first set of AEP signal data by applying a plurality of true random frequencies to the first set of AEP signal data to provide at least a second set of AEP signal data, (vi) recording the second set of AEP signal data, (vii) reconstructing the first waveform from the second set of AEP signal-data, and (viii) averaging the first set of OAE signal data to reconstruct the second waveform.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF PREFERRED EMBODIMENTS

The present invention substantially reduces or eliminates the disadvantages and drawbacks of prior art audiometric screening devices and methods. As discussed in detail below, except for subject preparation, the multi-mode audiometric screening device of the invention provides a fully automated screening procedure which includes stimulus presentation, multiple response signal acquisition, multiple signal analysis, and interpretation and display of results.

Figure 1:
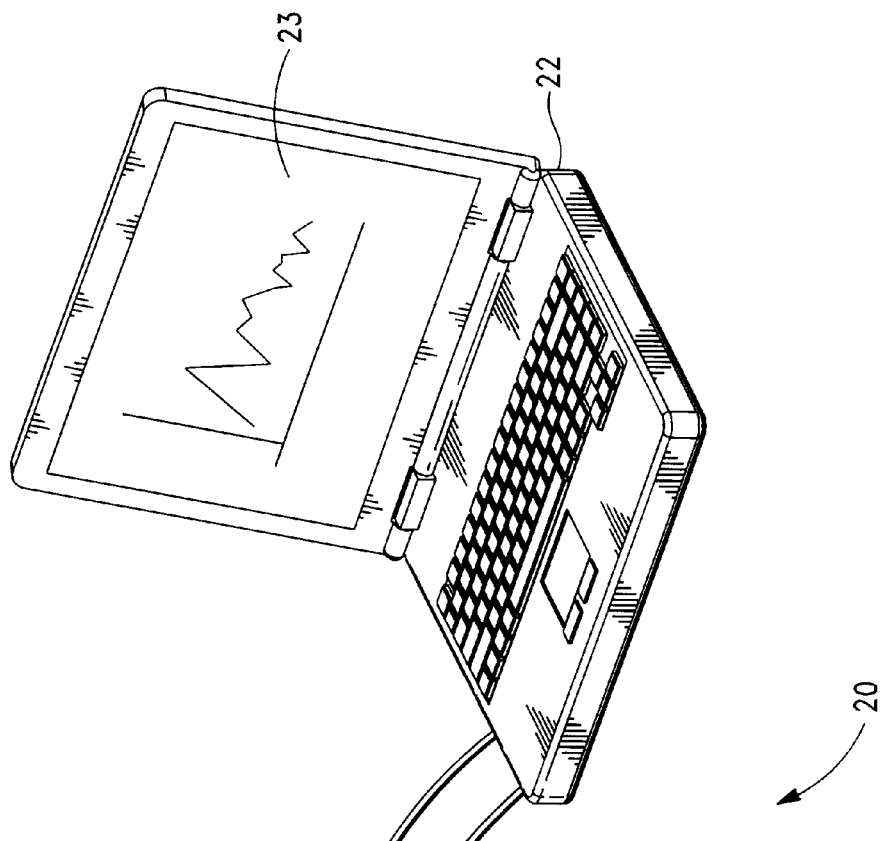
FIG. 1 is a schematic illustration of the multi-mode audiometric device according to the invention.

Referring first to FIG. 1, there is shown a preferred portable multi-mode audiometric screening system 20 incorporating the principals of the invention. The system 20 preferably includes a laptop computer 22 having control means 30 adapted to control the audiometric screening process, signal processing means 40 adapted to provide the unique "true random" stimulus signals and analyze the response signals emanating from the (infant) subject 10, and memory means 50 adapted to store pertinent data and information (see FIG. 2).

The audiometric screening system 20 further includes a probe 24 having an earphone 26 for presenting the acoustic stimulus signals generated by the signal processing means 40 to the subject 10. The earphone 26 also receives the OAE response signal from the subject's ear 12.

As illustrated in FIG. 1, the audiometric screening system 20 also includes a plurality of electrodes 28 that are operatively attached to the subject's scalp. According to the invention, the electrodes 28 sense and communicate the AEP or response signal to the signal processing means 40 of the invention.

In a preferred embodiment, one or more characteristics of the processed signals are displayed on the computer monitor 23. In additional embodiments of the invention, other pertinent information stored in the memory means 50 and/or provided by the signal processing means 40 is also displayed on the monitor 23.

Figure 2:
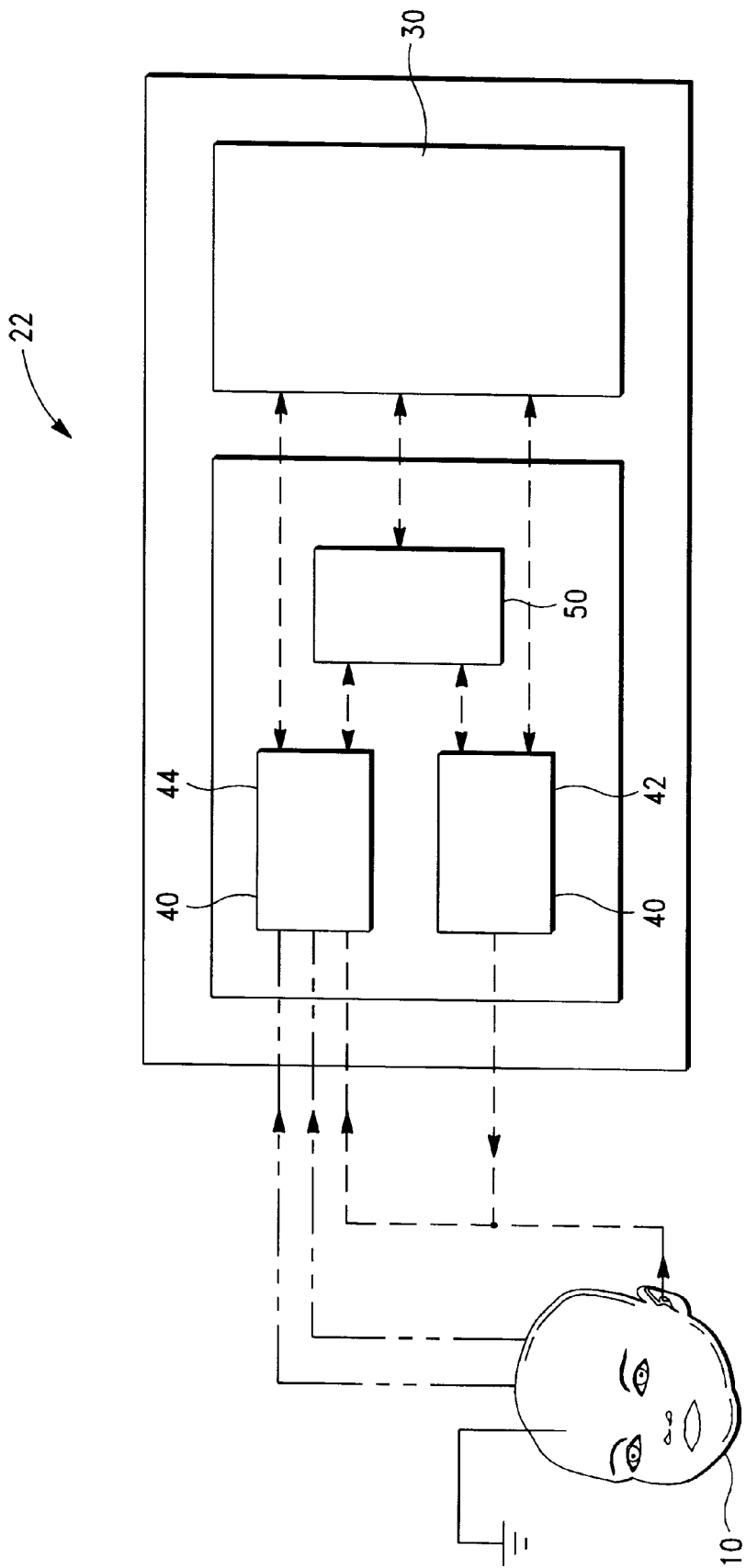
FIG. 2 is a block diagram of the multi-mode audiometric device according to the invention.

Referring now to FIG. 2, there is shown a block diagram of the audiometric screening system 20 shown in FIG. 1. As illustrated in FIG. 2, the laptop computer 22 preferably includes three primary components or systems: control means 30, signal processing means 40 and memory means 50.

The key component of the system 20 is, however, the signal processing means 40. In a preferred embodiment, the signal processing means 40 includes two subsystems: signal generator means 42 and signal analyzer means 44.

According to the invention, the signal generator means 42 provides a continuous, "true random" sequence—varying stimuli frequency and rate—that is presented to the subject via probe 24. As discussed in detail in application Ser. No. 09/782,503, filed Feb. 13, 2001, which is incorporated by reference herein, the "true random" sequence substantially reduces or eliminates "synchronous artifacts."

The "true random" sequence is preferably presented to the subject in the form of clicks or pulses—wide bandwidth, deterministic, short-duration signals. In prior art otoacoustic systems, the signal duration is typically limited by the duration of the impulse response of the acoustic source transducer, since the electrical input signal to the source transducer is typically much shorter than the impulse response duration. Thus, the stimulus duration is generally in the range of 80–100 msec, whereas the overall duration of the click-evoked otoacoustic emission (CEOAE) response is in the range of 10–40 msec.

Moreover, in U.S. Pat. No. 4,374,526 (Kemp) it is similarly assumed that the CEOAE response extends over a 20 msec interval. Kemp further states that the time interval between pulses should accordingly be at least 20 msec, corresponding to a presentation rate of 50 Hz (i.e., 50 clicks/sec), to prevent overlapping of the responses from succeeding pulse stimuli.

It has also been the overwhelming opinion of those having ordinary skill in the art that presenting a stimulus greater than 50 Hz results in a diminished electrical response (AEP). ABR testing thus typically employs a stimulus rate in the range of 35 to 40 Hz (e.g., 37 clicks/sec). Illustrative are the systems and techniques disclosed in U.S. Pat. No. 4,275,744.

Applicant has, however, found that a click-evoked AEP is not compromised or diminished until the stimulus rate is greater than approximately 200 Hz (i.e., 200 clicks/sec). Accordingly, in a preferred embodiment of the invention, the stimulus rate is in the range of 30 to 300, preferably 100 to 200 clicks/sec.

The variation in stimulus rate is also preferably maintained in the range of +/−10 to 50%. More preferably, the variation in stimulus rate is maintained in the range of +/−30 to 50%.

Analysis of the response signals—the OAE emanating from within the ear canal and AEP acquired from the scalp—is conducted by the signal analyzer means 44. According to the invention, the signal analyzer means 44 includes a plurality of signal sampling techniques and signal processing algorithms.

In a preferred embodiment of the invention, a "true random" sampling technique is employed to analyze and, hence, determine the waveform of the AEP signal resulting from the "true random" stimulus. Details of the "true random" sampling technique are similarly set forth in application Ser. No. 09/782,803, filed Feb. 13, 2001.

According to the invention, the signal analyzer means 44 also includes first averager means to read the spectral waveform that is produced by the noted random sampling technique. In a preferred embodiment, the first averager means comprises the "sampling averager" disclosed in the noted Co-Pending Application.

As discussed in detail in the noted Co-Pending Application, the "true random" sampling technique provides a reconstructed waveform that physiologically occurs in time intervals that are representative of the "actual" data emanating from the subject, without contamination from any extraneous, synchronous sources.

In contrast to the AEP signal, the acoustic response (OAE) comprises two distinct, "time-spaced" (i.e., synchronous) components, (i) a direct signal component and (ii) an echo signal component. The direct signal component represents the response of the ear drum and the middle ear, which typically terminates approximately 5 msec. after presentation of the stimulus. The echo signal component, which is more closely related to the characteristics and condition of the inner ear, typically terminates approximately 15 msec. thereafter.

Thus, according to the invention, the signal analyzer means 44 further includes synchronization means for synchronizing the signal generator means 42 and signal processing means 40. Since the noted OAE signal components are "time-spaced", but in synchrony, the echo signal component is readily separated and identified by the synchronization means. The echo signal component is then stored in the memory means 50 of the invention.

In a preferred embodiment, the signal analyzer means 42 additionally includes second averager means for reconstructing the OAE waveform. The second averager means is preferably adapted to be responsive to a sequence of 20–2000 echoes. According to the invention, the second averager means can comprise various conventional averagers and associated algorithms, such as the averager and associated ensemble averaging and group variance techniques disclosed in U.S. Pat. No. 5,601,091 and the averaging algorithm disclosed in U.S. Pat. No. 4,884,447 (Kemp); and deconvolution techniques, such as the MLS (pseudo-random) deconvolution technique disclosed in U.S. Pat. No. 5,734,827 (Thornton, et. al). In a preferred embodiment, the second averager means comprises a "true random" sequence deconvolution technique.

According to the invention, the AEP acquired from the subject 10, the data provided via the "true random" sampling technique and the reconstructed waveform determined therefrom, and the averaged OAE signal are stored in the memory means 50 of the system 20 for subsequent, separate analysis, if desired, and visual display on the monitor 23 for assessment.

As illustrated in FIG. 2, to control and monitor each of the above discussed features and/or components of the system 20 control means 30 are provided. In a preferred embodiment, the control means 30 comprises a microprocessor adapted to be programmed to perform a plurality of discreet and inter-related functions, including (i) control of the presentation of the stimuli, (ii) acquisition, processing and analysis of the noted response signals, (iii) input and extraction of information and data to/from the memory means 50 and (iv) display of desired information and/or data on the computer display 23. The control means are also adapted to be responsive to multiple user commands, including entry and storage of subject data and testing parameters. As will be appreciated by one having skill in the art, the noted control means 30 can also be programmed to perform numerous additional functions independently and in response to user commands.

As will be recognized by one having skill in the art, the above described multi-mode audiometric device and screening method provides numerous advantages over prior art devices and methods. The advantages include:

1. Simultaneous, comprehensive ABR and OAE testing through a single, portable device;
2. A significant reduction in response time (i.e. time to receive a response signal) and, hence, test time by virtue of the higher stimulus rate;
3. The virtual elimination of synchronous artifacts by virtue of the "true random" sequence presented to the subject; and
4. The virtual elimination of "sampling" artifacts from the AEP signal(s) by virtue of the random sampling technique of the invention.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A multi-mode audiometric apparatus for testing hearing, comprising:

stimulus generating means for transmitting at least one true random stimulus sequence to a subject's inner ear, said true random stimulus sequence having a first stimulus rate;

first detection means for detecting at least one auditory evoked potential (AEP) signal, said AEP signal having at least a first waveform, said first waveform including a plurality of AEP signal data;

second detection means for detecting at least one otoacoustic emission (OAE) signal, said OAE signal having at least a second waveform;

signal analyzer means for analyzing said AEP and OAE signals, said signal analyzer means including first averager means for reconstructing said first waveform, said first averager means including sampling means for sampling said first waveform, said sampling means including means for applying a plurality of true random frequencies to said plurality of AEP signal data to reconstruct said first waveform, said signal analyzer means further including second averager means for reconstructing said second waveform; and synchronization means for synchronizing said stimulus generating means and said signal analyzer means.

2. The apparatus of claim 1, wherein said apparatus includes control means for controlling said stimulus generating means.

3. The apparatus of claim 2, wherein said control means includes means for controlling said signal analyzer means.

4. The apparatus of claim 1, wherein said first stimulus rate is in the range of approximately 30–300 clicks/second.

5. The apparatus of claim 4, wherein said first stimulus rate is in the range of approximately 100–200 clicks/second.

6. The apparatus of claim 4, wherein a maximum variation in said first stimulus rate is in the range of approximately +/−10–50%.

7. A method of testing the hearing of a subject, comprising the steps of:

presenting at least one true random stimulus sequence to said subject's inner ear;

detecting at least one auditory evoked potential (AEP), said AEP signal having at least a first waveform, said first waveform including a first set of AEP signal data;

detecting at least one otoacoustic emission (OAE) signal, said OAE signal having at least a second waveform, said second waveform including a first set of OAE signal data;

recording said AEP and OAE signals;

sampling said first set of AEP signal data by applying a plurality of true random frequencies to said first set of AEP signal data, said sampling providing at least a second set of AEP signal data;

recording said second set of AEP signal data;

reconstructing said first waveform from said second set of AEP signal data; and averaging said first set of OAE signal data to reconstruct said second waveform.

* * * * *